United States Patent [19]

Frimer

[11] 4,376,733

[45] Mar. 15, 1983

[54] PREPARATION OF OXACYCLOALKENONES

[76] Inventor: Aryeh Frimer, 37 Hanasi Harishon St., Rehovot, Israel

[21] Appl. No.: 262,506

[22] Filed: May 11, 1981

[30] Foreign Application Priority Data

May 20, 1980 [IL]  Israel ........................................ 60122

[51] Int. Cl.$^3$ ............................................ C07D 313/06
[52] U.S. Cl. .................................... 549/268; 549/292; 549/275; 549/271
[58] Field of Search .................. 260/343, 343.5, 343.6, 260/343.41

[56] References Cited

U.S. PATENT DOCUMENTS 2,948,740  8/1960  Baran .............................. 260/397.4
3,128,283  4/1964  Pappo .............................. 260/343.41
3,644,342  2/1972  Chorvat et al. ................. 260/343.42

OTHER PUBLICATIONS

Kocor et al., Tetrahedron, vol. 25, pp. 4257–4264, 1969.

*Primary Examiner*—Jane T. Fan
*Attorney, Agent, or Firm*—Browdy and Neimark

[57] ABSTRACT

Oxacycloalkenones are prepared by reacting a cycloalkenone with a base in the presence of a dioxygen source in a suitable solvent and isolating the desired product. 1-Hydroxy 2-oxa-3-oxo-$\Delta^4$ steroids are convenient synthetic precursors to 2-oxa-3-oxo-$\Delta^4$ steroids which find use in modern clinical therapy.

19 Claims, No Drawings

PREPARATION OF OXACYCLOALKENONES

FIELD OF THE INVENTION

The present invention is concerned in general with a novel process for the preparation of 5-hydroxy-4-oxacycloalk-1-en-3-ones denoted by structure I

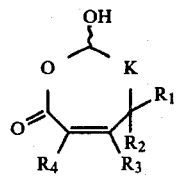

and particularly with the preparation of 1-hydroxy-2-oxa-3-oxo-$\Delta^4$ steroids denoted by the partial structure II

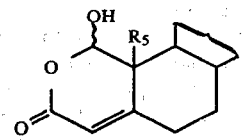

and with their 2-hydroxy-3-oxa-4-oxo-A-homo-$\Delta^{4a}$ steroidal analogs denoted by partial structure III.

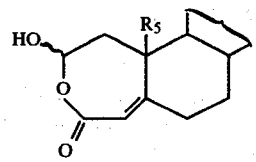

In the above structures $R_1$ and $R_2$ are typically hydrogen, alkyl or aryl radicals, $R_3$ and $R_4$ are generally hydrogen, alkyl, aryl or alkoxy radicals, $R_5$ is an optionally substituted methyl group and K is a hydrocarbon chain with optional unsaturation or substitution.

BACKGROUND OF THE INVENTION

The use of steroidal hormones is well known in modern clinical therapy. Examples of such hormones are corticoids, anabolic agents and various progesterones. However, the useful properties of these drugs are usually accompanied by undesirable activities or side effects. As a result, a variety of heterosteroids have been synthesized in the hope that the undesired properties could be separated from the desired effects.

Some success has indeed been observed in the case of 2-oxasteroids. [For reviews see R. Pappo, Intra-Science Chemistry Reports, 3, 105 (1969) and H. Singh et al., Prog. Med. Chem., 16, 35 (1979)]. For example in the heteroprogesterone series, 2-oxaprogesterone and its 17α-acetoxy analog are almost as active as progesterone and 17α-acetoxyprogesterone. In the cortisone series, 3-oxa-A-homo-11-hydrocortisone is at least as active as hydrocortisone and does not show salt retaining properties.

One of the most convenient methods of synthesizing 2-oxa-3-oxo-$\Delta^4$-steroids (VI) is by reducing the corresponding 1-hydroxy-2-oxa-3-oxo-$\Delta^4$-steroids (II) as outlined below.

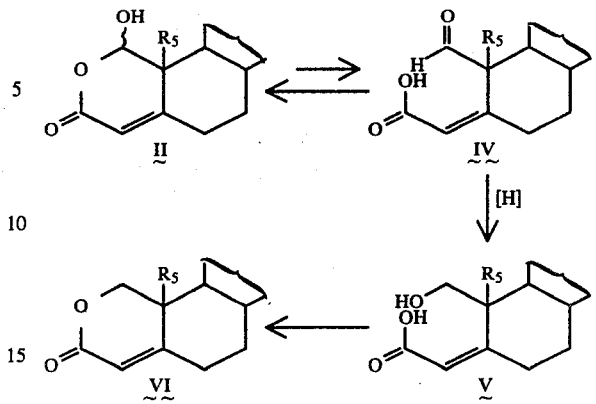

As shown, compounds of type II are hydroxy-lactones or lactols which are in equilibrium with the A-nor-1,2-seco aldehydo acid form IV. The latter is reduced, typically by sodium borohydride, to the corresponding 8-hydroxy acid V which readily dehydrates in turn yielding a lactone VI which is the desired 2-oxa-3-oxo-$\Delta^4$-steroid. A similar approach is applicable to the 3-oxa-A-homo series.

Methods of synthesizing 1-hydroxy-2-oxa-3-oxo-$\Delta^4$ steroids (VI) are known in the prior art. Each of these methods suffers from a variety of shortcomings. For example, a method described in U.S. Pat. No. 3,128,283 is a multistep process which involves the use of the expensive and toxic reagents osmium tetroxide and lead tetraacetate. Another approach, described in U.S. Pat. No. 3,644,342 involves the ozonolysis of the electron rich enolic double bond of 2-hydroxy-3-oxo-$\Delta^{1,4}$ steroids. However ozone is a very vigorous oxidizing agent and can well attack other olefinic sites and functional groups in the substrate. Furthermore the substrate itself needs to be synthesized from the corresponding 3-oxo-$\Delta^4$-steroid. The method of Kocor et al. [Tetrahedron, 25, 4257 (1969)] involves the oxidation of a 3-oxo-$\Delta^{1,4}$ steroid with alkaline hydrogen peroxide and involves the intermediacy of the corresponding 1,2-epoxide. This method requires the prior synthesis and isolation of the 3-oxo-$\Delta^{1,4}$ steroid from the corresponding $\Delta^4$ -steroidal analog and thus introduces an additional step into the synthetic scheme.

A method has been reported [R. Hanna and G. Ourisson, Bull. Soc. Chim. Fra., 1945 (1961)] in which 3-oxosteroids saturated at the 4-carbon have been converted into the corresponding lactol, 1-hydroxy-2-oxa-3-oxo-steroid, either directly or via the intermediacy of the corresponding enol, 2-hydroxy-3-oxo-$\Delta^1$-steroid, by the action of potassium t-butoxide in protic media (butanol-benzene solvent mixture) under a molecular oxygen atmosphere. However, it has been recently reported [R. J. Chorvat and R. Pappo, J. Org. Chem., 41, 2864 (1976)] that this method is unsuitable for the preparation of the unsaturated $\Delta^4$-lactols of type II.

SUMMARY OF THE INVENTION

The present invention overcomes these difficulties and describes an economical, convenient and direct synthetic route to lactols of type I from the corresponding cycloalkenones of type VII or VIII, as outlined below. In particular this method is useful for the preparation of hydroxy oxasteroids of type II and III.

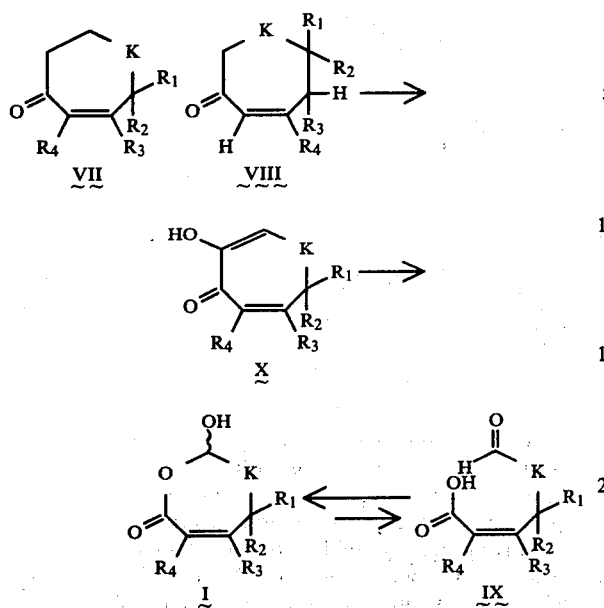

In accordance with an embodiment of the present invention cycloalkenone is reacted with base in the presence of a dioxygen source. The dioxygen source may be any species or mixture which supplies the elements of $O_2$ for the reaction. Typical dioxygen sources are air, molecular oxygen ($O_2$) in its ground or excited states, hydrogen peroxide ($H_2O_2$), hydroperoxide anion or radical ($HOO^-$ or $HOO^\bullet$), superoxide anion ($O_2^-$) and peroxide dianion $O_2^{-2}$. Typical bases are potassium or sodium superoxide, potassium or sodium hydroxide, Triton B (N-benzyltrimethylammonium hydroxide), potassium t-butoxide, sodium methylsulfinylmethide (dimsyl sodium), potassium or sodium hydride, but clearly other strong bases can be as effective. It is clear that in certain cases the base might also serve as the dioxygen source (e.g. potassium superoxide). The base is normally present in excess and a typical molar ratio of base to phase transfer agent to substrate is 6:3:2. The reaction is generally conducted at room temperature. The duration of the reaction typically varies from 12 to 72 hours and depends on a variety of factors, such as the nature of the substrate, base and solvent as well as on the concentration of the reactants.

In the preferred embodiment of this invention, the reaction is carried out in dry inert aprotic solvent typically benzene, toluene, and similar alkyl and halobenzenes, alkylamines, dimethylformamide, hexamethylphosphoramide, ethers, acetonitrile, dimethylsulfoxide or pyridine. When using such solvents it is usually necessary to add a phase transfer agent to aid in solubilizing the base. Typical phase transfer agents are quarternary ammonium salts, crown ethers, cryptants and linear polyethers. (The publication "Compendium of Phase Transfer Reactions and Related Synthetic Methods" by W. E. Keller, Fluka AG, 1979 Switzerland discloses a large number of such phase transfer agents.)

While the final product is the desired lactol $I$, as outlined above the reaction proceeds via the intermediacy of the corresponding enol $X$ which is generated in situ and may be isolated if so desired. Thus this method may be used to synthesize enol $X$ provided the reaction is terminated at the appropriate time. It is a particular feature of this method for the synthesis of enol $X$ that enones of type $VII$ or $VIII$ are contacted with base in an aprotic solvent. Enol $X$, synthesized by this or alternate methods (see for example U.S. Pat. Nos. 3,644,342 and 2,948,740), may itself serve as substrate for this method of synthesizing lactols of type $I$. Nevertheless in its preferred embodiment, the present invention is a "one-pot" method leading directly from cycloalkenone ($VII$ or $VIII$) to the desired lactol ($I$) and does not require preparation and isolation of the corresponding enol ($X$). Thus it is a particular feature of this invention that it allows for the preparation of 2-oxa-3-oxo-$\Delta^4$ steroids ($VI$) from the readily available 3-oxo-$\Delta^4$ steroids in just two synthetic steps, the first leading directly to lactol $II$ and the second to desired lactone $VI$.

DETAILED DESCRIPTION OF THE INVENTION

The invention will be more fully appreciated from the examples which follow. These examples are given by way of illustration only and are not to be construed as limiting the invention either in spirit or in scope, as many modifications both in materials and methods will be apparent to those skilled in the art. In these examples quantities of materials are given in parts by weight except where otherwise noted. Preparative thin layer chromatography (TLC) was carried out on silica plates. Nuclear agnetic resonance (NMR) data are given in parts per million using tetramethylsilane as the reference. Preparative vapor phase chromatography (VPC) was carried out on a column containing 20% Carbowax on Chromosorb WAWDMCS.

EXAMPLE 1

A solution of 1 part 4, 4-diphenylcyclohex-2-en-1-one, one part of either potassium superoxide or potassium hydroxide and 2 parts 18-crown-6 in 200 parts of benzene is stirred for 16 hours at room temperature either in dry air or an oxygen atmosphere. In the potassium superoxide case the reaction can also be run in an argon atmosphere. The reaction mixture is neutralized with dilute acid and washed with sodium bicarbonate solution to remove acidic products. The organic layer is dried over magnesium sulfate and the solvent is removed under vacuum. The product is purified by preparative TLC with benzene as eluent. Recrystallization from a benzene-petroleum ether solvent mixture yielded pure crystals of 2-hydroxy-4,4-diphenylcyclohexa-2,5-dien-1-one melting at 145° C. This compound was characterized by a correct elemental analysis (calculated: C-82.44, H-5.34; Experimental: C-82.21, H-5.42) and by its spectral data: $^1H$ NMR (CDCl$_3$) $\delta$ 6.35 (d, J=10 Hz, 1H) 6.50 (s, 1H); 7.33 (m, 12H); IR (Nujol) 3360 and 1640 cm$^{-1}$; M.S. (70 ev) m/e 262 (M+).

EXAMPLE 2

A solution of 1 part 4,4-dimethylcyclohex-2-en-1-one, 2 parts potassium superoxide and 4 parts 18-crown-6 in 200 parts benzene is stirred for 5 hours in dry air and worked-up in the usual manner. The product, 2-hydroxy-4,4-dimethylcyclohexa-2,5-dien-1,-one, was purified by preparative VPC. The same product is obtained when 1.6 parts of potassium hydroxide are employed instead of potassium superoxide; however, in this case it is necessary to allow the reaction to continue for 16 hours prior to work-up. The enol was characterized by its spectral data: $^1H$ NMR (CDCl$_3$) $\delta$ 1.27 (s, 6H) 6.07 (d, 1H, J=3Hz) 6.18 (d, 1H, J=10Hz) 6.90

(dd,1H,J=10 and 3Hz); IR (CDCl$_3$) 3400 and 1640 cm$^{-1}$; MS (70 ev) m/e 138 (M+).

EXAMPLE 3

A solution of 1 part 5,5-dimethylcyclohex-2-en-1-one, 2 parts 18-crown-6 and 1 part potassium superoxide in 200 parts benzene is stirred for 7 hours under dry air and worked-up in the usual manner. The product proved to be the same enol obtained in example 2. This enol was also obtained when potassium hydroxide replaced potassium superoxide, but here the reaction is allowed to continue for 16 hours prior to work up.

EXAMPLE 4

A solution of 1 part 2-hydroxy-4,4-dimethylcyclohexa-2,5-dien-1-one, 1 part potassium superoxide and 2 parts 18-crown-6 in 200 parts benzene is stirred for 5 hours under dry air, neutralized and extracted with sodium bicarbonate solution. The aqueous extracts are acidified and the organic porduct is extracted into chloroform. The organic layer is dried over magnesium sulfate and evaporation of the solvent under vacuum yields 5-hydroxy-4,4-dimethyl-6-oxacyclohex-2-en-1-one. This lactol can also be obtained directly from 4,4-dimethylcyclohex-2-en-1-one, by stirring one part of the latter with 4 parts of 18-crown-6 and 2 parts potassium superoxide in 200 parts benzene for 16 hours. The lactol likewise results directly when 1 part 5,5-dimethylcyclohex-2-en-1-one, 2 parts potassium superoxide and 4.5 parts 18-crown-6 are reacted in 200 parts benzene for 16 hours. The lactol is characterized by its spectral data: $^1$H NMR (CDCl$_3$) $\delta$ 1.18 (s,6H) 5.36 (s,1H) 5.90 (d,J=13 Hz,1H) 6.56 (d,J=13 Hz, 1H); IR (CHCl$_3$) 3380, 1720 and 1640 cm$^{-1}$.

EXAMPLE 5

A solution of 1 part 3,5,5-trimethylcyclohex-2-en-1-one, 2 parts potassium superoxide and 4 parts 18-crown-6 in 200 parts benzene was stirred for 2 hours under dry air and worked-up in the usual manner. The product, 2-hydroxy-4,4,6-trimethylcyclohexa-2,5-dien-1-one has a melting point at 57° and was identified by its spectral data: $^1$H NMR (CDCl$_3$) $\delta$ 1.24 (s,6H) 1.90 (d,J=2 Hz3H) 6.30 (s,1H) 5.93 (d,J=4,1H) 6.64 (m,1H); IR (CHCl$_3$) 3420, 1640, and 1620 cm$^{-1}$, MS (70 ev) m/e 152 (M+).

When 1 part of this enol is stirred for 16 hours with 1 part potassium superoxide and 2 parts 18-crown-6 in 250 parts benzene, 5-hydroxy-2,4,4-trimethyl-6-oxacyclohex-2-en-1-one is obtained after the usual work-up. This lactol is characterized by its spectral data: $^1$H NMR (CDCl$_3$) $\delta$ 1.15 (s,6H) 1.88 (d,J=3 Hz,3H) 5.36 (s,1H) 6.30 (bs,1H); IR (CHCl$_3$) 3420, 1700, 1640 cm$^{-1}$.

To further verify the structure of the lactol, the latter was reacted with excess diazomethane, yielding the methyl ester of the aldehyde acid form IX. Methyl 2,4,4-trimethyl-5-oxo-cis-2-pentenoate was characterized by its spectral data: $^1$H NMR (CDCl$_3$) $\delta$ 9.47 (s,1H) 5.87 (bs,1H) 3.66 (s,3H) 1.96 (bs,3H) 1.23 (s,6H): IR (neat) 2700, 1270, 1630 cm$^{-1}$.

EXAMPLE 6

A solution of 1 part 3-ethoxy-5,5-dimethylcyclohex-2-en-1-one, 3 parts potassium hydroxide and 3 parts 18-crown-6 in 200 parts benzene was stirred for 7 hours under dry air and worked up in the usual manner. The product 2-ethoxy-6-hydroxy-4,4-dimethylcyclohexa-2,5-dien-1-one melted at 82° C. and was identified by its spectral data: $^1$H NMR (CDCl$_3$) $\delta$ 1.26 (s,6H), 1.33 (t,J=10 Hz,3H) 3.76 (q,J=10H$_3$, 2H) 6.23 (s,1H) 5.76 (d,J=3 Hz,1H) 6.00 (d,J=3 Hz,1H); IR (CCl$_4$) 3420,1620 and 1590 cm$^{-1}$; MS (70 ev) m/e 182 (M+); $^{13}$C NMR (CDCl$_3$) $\delta$ 14.28, 28.68, 36.13, 63.65, 125.72, 128.29, 145.43, 145.94, 177.60.

When the reaction solution is stirred for 72 hours prior to work up, 2-ethoxy-5-hydroxy-4,4-dimethyl-6-oxacyclohex-2-en-1-one is produced. This lactol is also obtained when 1 part of either 3-ethoxy-5,5-dimethylcyclohex-2-en-1-one or 2-ethoxy-6-hydroxy-4,4-dimethylcyclohexa-3,5-dien-1-one is stirred 16 hours with 1.5 parts potassium hydroxide and 3 parts 18-crown-6 in 200 parts benzene. The lactol was characterized by its spectral data: $^1$H NMR (CDCl$_3$) $\delta$ 1.17 (s,6H) 1.37 (t,J=10 Hz,3H) 3.80 (q,J=10 Hz,2H) 5.26 (s,1H) 5.36 (s,1H); IR (CHCl$_3$) 3360, 1720 and 1630 cm$^{-1}$; $^{13}$C NMR (CDCl$_3$) $\delta$ 13.18, 20.51, 24.90, 35.71, 63.05, 100.83, 118.59, 141.66, 160.65.

To further verify the structure of the lactol, the latter was reacted with excess diazomethane yielding methyl 2-ethoxy-4,4-dimethyl-5-oxo-cis-2-pentenoate. This aldehydo ester was identified by its spectral data: $^1$H NMR (CDCl$_3$) $\delta$ 9.47 (s,1H) 5.10 (s,1H) 3.73 (s,3H) 3.80 (q,J=10 Hz,2H) 1.36 (t,J=10 Hz,3H) 1.25 (s,6H); IR (neat) 2700, 1379, 1620 cm$^{-1}$; MS (70 ev) m/e 172 (M+ −28).

Acetylation of the lactol with acetic anhydride-pyridine yielded 5-acetoxy-2-ethoxy-4,4-dimethyl-6-oxacyclohex-2-en-1-one which was characterized by elemental analysis (calculated: C—57.89, H—7.01; experimental: C—57.90, H—7.16) and spectral data: $^1$H NMR (CDCl$_3$) $\delta$ 6.20 (s,1H) 5.35 (s,1H) 3.80 (q,J=12 Hz,2H) 2.10 (s,3H) 1.40 (t,J=12,3H) 1.23 (s,3H) 1.17 (s,3H); IR (CHCl$_3$) 1760, 1730, 1640 cm$^{-1}$; UV (Ethanol): $\lambda_{max}$=248, $\Sigma_{max}$=7637 mol−cm$^2$; MS (70 ev) m/e 228 (M+).

This lactol is converted to the corresponding lactone, 2-ethoxy-4,4-dimethyl-6-oxacyclohex-2-en-1-one, as follows. To a solution containing one part lactol, 15 parts 0.5 N sodium hydroxide, 480 parts methanol and 600 parts water, was added 1.3 parts sodium borohydride in 30 parts water. The solution was left at room temperature for 16 hours and acidified with 10% HCl. The product was then extracted into chloroform. The chloroform solution was dried over magnesium sulfate and the solvent was subsequently removed in vacuo. Preparative TLC yielded pure lactone with the following spectral data: $^1$H NMR (CDCl$_3$) $\delta$ 5.40 (s,1H) 3.97 (s,2H) 3.73 (q,J=10 Hz,2H) 1.33 (t,J=10 Hz,3H) 1.13 (s,6H); IR (neat) 1720 and 1630 cm$^{-1}$; MS (70 ev) m/e 170 (M+).

EXAMPLE 7

A solution of 2 parts 4-cholesten-3-one, 2 parts 18-crown-6 and 1.5 parts potassium t-butoxide in 400 parts benzene was stirred for 30 minutes at room temperature under an oxygen atmosphere and worked up in the usual manner. The product, 2-hydroxycholesta-1,4-dien-3-one, was purified by preparative TLC recrystallized from ligroin [M.P. 112.5–113.5] and identified by its spectral data: $^1$H NMR (CDCl$_3$) $\delta$ 6.13 (s,H-4) 6.30 (s,H-1); MS (70 ev)m/e 398 (M+); IR (CHCl$_3$): 3420, 1620, 1605 cm$^{-1}$. The same enol was obtained when a solution of 1.7 parts of 4-cholesten-3-one, 2.4 parts of 18-crown-6 and 1 part of potassium hydroxide in 350 parts benzene was stirred for 3 days at room temperature under an oxygen atmosphere and worked up in the usual manner. The rate of reaction in this and similar cases can be increased if the oxygen pressure is increased above one atmosphere.

If the potassium t-butoxide reaction is allowed to proceed for 24 hours before work-up, 1-hydroxy-2-oxa-cholest-4-en-one is obtained. This lactol also results when 1 part potassium superoxide replaces potassium t-butoxide and the reaction mixture is stirred 3 days before quenching. Alternatively the lactol may be prepared by stirring a mixture of 1.5 parts 4-cholesten-3-one and 1 part potassium superoxide in 300 parts of dimethylsulfoxide. Similarly, the lactol may be prepared by stirring a solution of 1 part 4-cholesten-3-one and 4 parts 40% methanolic Triton B solution in 300 parts benzene under an oxygen atmosphere for 2 days. As before, the enol once isolated may also be readily converted to the lactol. The lactol was characterized by its spectral data: $^1$H NMR (CDCl$_3$) δ 5.67 (s,H−4) 5.38 (s,H−1); IR (CHCl$_3$) 3360, 1690, 1640 cm$^{-1}$; MS (40 ev) m/e 402 (M+). M.P. 135° (Ether-Ligroin).

The lactol was further characterized by preparing the methyl ester of the corresponding aldehydo acid form IV. Reaction of the lactol with diazomethane yielded methyl 1-oxo-1,2-seco-A-norcholest-3-en-2-oate which was characterized by its spectral data: $^1$H NMR (CDCl$_3$) δ 9.36 (s,1H) 5.70 (s,1H) 3.60 (s,1H) MS (70 ev) m/e 416 (M+); IR (CHCl$_3$) 2730, 1700, 1620 cm$^{-1}$.

The lactol may be reduced to the corresponding 2-oxa-Δ$^4$ steroid, 2-oxacholest-4-en-3-one, by reacting the former with sodium borohydride in a fashion analogous to that described in Example 6. The lactone is characterized by its spectral data: $^1$H NMR (CDCl$_3$) δ 5.57 (s,H−4) 4.20 and 3.94 (Ab−q,J=13 Hz,2H,H−1); MS (70 ev) m/e 386 (M+); IR (CHCl$_3$): 1700, 1630 cm$^{-1}$.

EXAMPLE 8

A solution of 20 parts testosterone, 27 parts 18-crown-6 and 23 parts potassium t-butoxide in 5600 parts benzene was stirred for 10 minutes under an oxygen atmosphere and worked up in the usual manner. The product was purified by preparative TLC and identified as 2-hydroxy-1,2-dehydrotestosterone based on its spectral data: $^1$H NMR (CDCl$_3$) δ 6.13 (s,H−4) 6.30 (s,H−1) 3.63 (t,J=11 Hz,H−17) 1.20 (s,3H) 0.80 (s,3H); IR (CHCl$_3$): 3420, 1635, 1610 cm$^{-1}$; MS (70 ev) 302 (M+).

If the reaction is allowed to proceed for 3 days prior to work up 1-hydroxy-2-oxatestosterone is obtained. This lactol also results when a solution of 1 part testosterone, 2 parts 18-crown-6 and 1 part potassium superoxide in 250 parts benzene is stirred for 3 days under an oxygen atmosphere and worked up in the usual manner. As before the isolated enol could also be transformed to the corresponding lactol. The lactol is characterized by its spectral data: $^1$H NMR (Methanol-d$_4$) 5.60 (s,H−4) 5.33 (s,H−1) 3.57 (t,J=12 Hz,H−17) 1.22 (s,3H) 0.77 (s,3H); IR (Nujol): 3330, 1680, 1635 cm$^{-1}$; MS (40 ev) 306 (M+).

I claim:

1. A process for the production of 1-hydroxy-2-oxa-3-oxo-Δ$^4$ steroid which comprises contacting a 3-oxo-Δ$^4$ steroid with a base in the presence of a dioxygen source in a suitable solvent and isolating the desired product.

2. A process according to claim 1 wherein the 3-oxo-Δ$^4$ steroid is a 2-hydroxy-3-oxo-Δ$^{1,4}$ steroid.

3. A process for the production of 2-oxa-3-oxo-Δ$^4$ steroid which comprises contacting a 3-oxo-Δ$^4$ steroid with a base in the presence of a dioxygen source in a suitable solvent to produce a 1-hydroxy-2-oxa-3-oxo-Δ$^4$ steroid, isolating the 1-hydroxy-2-oxa-3-oxo-Δ$^4$ steroid, contacting the 1-hydroxy-2-oxa-3-oxo-Δ$^4$ steroid with a metallic reducing agent and isolating the corresponding 2-oxa-3-oxo-Δ$^4$ steroid.

4. A process according to claim 3 wherein the 3-oxo-Δ$^4$ steroid is a 2-hydroxy-3-oxo-Δ$^{1,4}$ steroid.

5. The process according to any of claims 1, 2, 3 or 4 in which the solvent is an aprotic solvent.

6. The process according to any of claims 1, 2, 3 or 4 wherein the solvent is selected from a group of aprotic organic solvents comprising aromatic hydrocarbons, acetonitrile, dimethylsulfoxide, dimethylformamide, alkyl amines, hexamethylphosphoramide and ethers.

7. The process according to any of claims 1, 2, 3 or 4 wherein the solvent is an aprotic aromatic hydrocarbon selected from the group comprising benzene, toluene, xylene, mesitylene, ethylbenzene, halobenzenes and pyridine.

8. The process according to any of claims 1, 2, 3 or 4 wherein the base comprises an anion selected from the group comprising aryloxide, alkoxide, superoxide, hydroperoxide, hydroxide, alkylsulfinylmethide and hydride.

9. The process according to any of claims 1, 2, 3 or 4 wherein the reaction is carried out in the presence of a phase transfer agent.

10. The process according to any of claims 1, 2, 3 or 4 wherein the reaction is carried out in the presence of a phase transfer agent selected from the group comprising quarternary ammonium salts, crown ethers, cryptants and linear polyethers.

11. The process according to any of claims 1, 2, 3 or 4 wherein the dioxygen source is selected from the group comprising air, molecular oxygen, hydrogen peroxide, hydroperoxide anion, hydroperoxide radical, peroxide dianion and superoxide anion.

12. The process according to claim 3 wherein the 3-oxo-Δ$^4$ steroid is cholest-4-en-3-one; wherein the 1-hydroxy-2-oxa-3-oxo-Δ$^4$ steriod is 1-hydroxy-2-oxacholest-4-en-3-one; and wherein the 2-oxa-3-oxo-Δ$^4$ steriod is 2-oxacholest-4-en-3-one.

13. The process according to claim 3 wherein the 3-oxo-Δ$^4$ steroid is 2-hydroxycholesta-1,4-dien-3-one; wherein the 1-hydroxy-2-oxa-3-oxo-Δ$^4$ steroid is 1-hydroxy-2-oxacholest-4-en-3-one; and wherein the 2-oxa-3-oxo-Δ$^4$ steroid is 2-oxacholest-4-en-3-one.

14. The process according to claim 3 wherein the 3-oxo-Δ$^4$ steroid is testosterone; wherein the 1-hydroxy-2-oxa-3-oxo-Δ$^4$ steroid is 1-hydroxy-2-oxatestosterone; and wherein the 2-oxa-3-oxo- Δ$^4$ steroid is 2-oxatestosterone.

15. The process according to claim 3 wherein the 3-oxo-Δ$^4$ steroid is 2-hydroxy-1,2-dehydrotestosterone; wherein the 1-hydroxy-2-oxa-3-oxo-Δ$^4$ steroid is 1-hydroxy-2-oxatestosterone; and wherein the 2-oxa-3-oxo-Δ$^4$ steroid is 2-oxatestosterone.

16. The process according to claim 3 wherein the 3-oxo-Δ$^4$ steroid is a 4-oxo-Δ$^{4a}$-A-homosteroid; wherein the 1-hydroxy-2-oxa-3-oxo-Δ$^4$ steroid is a 2-hydroxy-3-oxa-4-oxo-Δ$^{4a}$-A-homo steroid; and wherein the 2-oxa-3-oxo-Δ$^4$ steroid is a 3-oxa-4-oxo-Δ$^{4a}$-A-homo steroid.

17. The process according to claim 3 wherein the 3-oxo-Δ$^4$ steroid is a 3-hydroxy-4-oxo-A-homoΔ$^{2,4a}$ steroid; wherein the 1-hydroxy-2-oxa-3-oxo- Δ$^4$ steroid is a 2-hydroxy-3-oxa-4-oxo-$\Delta^{4a}$-A-homo steroid; and wherein the 2-oxa-3-oxo-$\Delta^4$ steroid is a 3-oxa-4-oxo-$\Delta^{4a}$-A-homo steroid.

18. A process for the production of 2-oxacholest-4-en-3-one which comprises the steps of contacting cholest-4-en-3-one with potassium superoxide in benzene containing 18-crown-6, reacting the resulting 1-hydroxy-2-oxacholest-4-en-3-one with sodium borohydride, and isolating the 2-oxacholest-4-en-3-one.

19. A process for the production of 2-oxatestosterone which comprises the steps of contacting testosterone with potassium superoxide in benzene containing 18-crown-6, reacting the resulting 1-hydroxy-2-oxatestosterone with sodium borohydride, and isolating the 2-oxatestosterone.

* * * * *